US00PP09114P

United States Patent [19]

Zary

[11] Patent Number: Plant 9,114

[45] Date of Patent: Apr. 25, 1995

[54] SHRUB ROSE PLANT NAMED 'JACTORBO'

[75] Inventor: Keith W. Zary, Thousand Oaks, Calif.

[73] Assignee: Bear Creek Gardens, Inc., Medford, Oreg.

[21] Appl. No.: 150,681

[22] Filed: Nov. 9, 1993

[51] Int. Cl.[6] ..... A01H 5/00

[52] U.S. Cl. ..... Plt./1

[58] Field of Search ..... Plt. 1, 3

*Primary Examiner*—Howard J. Locker

*Attorney, Agent, or Firm*—Klarquist Sparkman Campbell Leigh & Whinston

[57] ABSTRACT

Rose plant of shrub class that roots readily as softwood or hardwood cuttings; is compatible with various scion-wood as rootstock; and has a vigorous and healthy growth, with large, arching canes that are excellent sources of rootstock cuttings.

1 Drawing Sheet

The present invention relates to a new and distinct variety of rose plant of the shrub class which was originated by me by crossing an unnamed seedling, with an unnamed cultivar of the species, *R. indica* major (odorata).

The primary objective of this breeding was to produce a new rose variety having the same or better rooting percentage, ease of grafting and disease resistance as the pollen parent which is an excellent source of rootstock, combined with the improved powdery mildew resistance and longer canes of the unnamed female climbing rose parent. The objective was substantially achieved, along with other desirable improvements, as evidenced by the following unique combination of characteristics that are outstanding in the new variety and that distinguish it from its parents, as well as from all other varieties of which I am aware:

1. Readily roots as both softwood and hardwood cuttings;
2. Has excellent disease resistance;
3. Produces vigorous plants when used as an understock;
4. Shows wide graft capability with various scion-wood when used as an understock;
5. Produces large, vigorous foliage; and
6. Develops long, arching canes that are ideal as sources of rootstock cuttings.

Asexual reproduction of this new variety by softwood and hardwood cuttings as performed at Wasco and Somis, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—*R. indica* major (odorata).

Classification:

*Botanical.*—*Rosa hybrida.*

*Commercial.*—Shrub.

FLOWER

Observations made from specimens grown in garden and greenhouse environments in both Wasco and Somis, Calif.

Blooming habit: Spring (only on 2-year-old wood).

Bud:

*Size.*—½ inch long when the petals start to unfurl.

*Form.*—Short, pointed ovoid.

*Color.*—When sepals first divide, bud color is White Group 155D. When half blown, the upper and lower sides of the petals are White Group 155D.

*Sepals.*—Color; Green Group 138B. Surface texture; Covered in fine hairs. There are three normally appendaged sepals. There are two unappendaged sepals with hairy edges.

*Receptacle.*—Color; Green Group 137C. Shape: Apple. Size: Small (⅛ inch×⅛ inch). Surface: Smooth.

*Peduncle.*—Length: Short (1 inch). Surface: Smooth. Color: Medium green. Strength: Stiff, erect, slender.

Bloom:

*Size.*—Small. Average open size is 2 inches in diameter.

*Borne.* —Several together and in large, rounded clusters with 8 to 15 flowers.

*Stems.*—Very long (up to 15 feet) and bending.

*Form.*—When first open: Cupped. Permanence: Flattens.

*Petalage.*-Number of petals under nomral conditions: 5 to 10.

*Color.*—The upper and reverse sides of the petals are White Group 155B. The base of each petal is white. The major color on the upper side is White Group 155B.

*Variegations.*—None.

*Discoloration.*—The general tonality at the end of the first and third days: No change.

*Fragrance:* Moderate.

Petals:

*Texture.*—Thin.

*Shape.*—Oval and notched.

*Form.*—Flat.

*Arrangement.*—Imbricated, with few petaloids in the center.

*Persistence.*—Drop off cleanly.

*Lastingness.*—On the plant: Short (3 days). As a cut flower: Short (3 days).

Reproductive parts:

*Anthers.*—Size; Small. Quantity: Many. Color: Yellow. Arrangement: Regular around styles.

*Filaments.*—Color: White.

*Pollen.*—Color: Gold-Yellow.

*Styles.*—Color: White.

*Stigmas.*—Color: Greenish-White.

form: Shrub or climber.

Growth: Very vigorous; upright, then arching into a large shrub (one 6 feet tall) could be trained as a climber.

Foliage: Number of leaflets on normal mid-stem leaves:

*Size.*—Large (6 inches long×4 inches wide).

*Quantity.*—Normal.

*Color.*—New foliage: Green Group 137C with a reddish cast on emerging leaves. Old foliage: Green Group 137A.

Leaflets:

*Shape.*—Pointed oval.

Texture.—Upper side: Leathery.

*Edge.*—Serrated.

*Serration.*—Single and small.

*Petiole rachis.*—Color: Reddish when young, becoming green.

*Petiole underside.*—Smooth with a few glands.

*Stipules.*—Medium (about ½ inch).

*Disease resistance.*—Resistant to mildew and rust under normal growing conditions at Somis, Calif.

Wood:

*New wood.*—Color; Reddish. Bark: Smooth.

*Old wood.*—Color: Green. Bark: Smooth.

Prickles:

*quantity.*—on main canes from base: Few, with one or two per node of growth. On laterals from main canes: Few.

*Form.*—Hooked downward.

*Color when young.*—Red.

Small prickles:

*Quantity.*—None on main stalks or laterals.

I claim:

1. A new and distinct variety of rose plant of the shrub class, substantially as herein shown and described, characterized particularly as to novelty by the unique combination of its ability to root readily as a softwood or hardwood cutting; its compatibility as a rootstock with various scionwood; its vigorous and healthy growth; its large foliage; and its long, arching canes that are excellent sources of new rootstock cuttings.

* * * * *

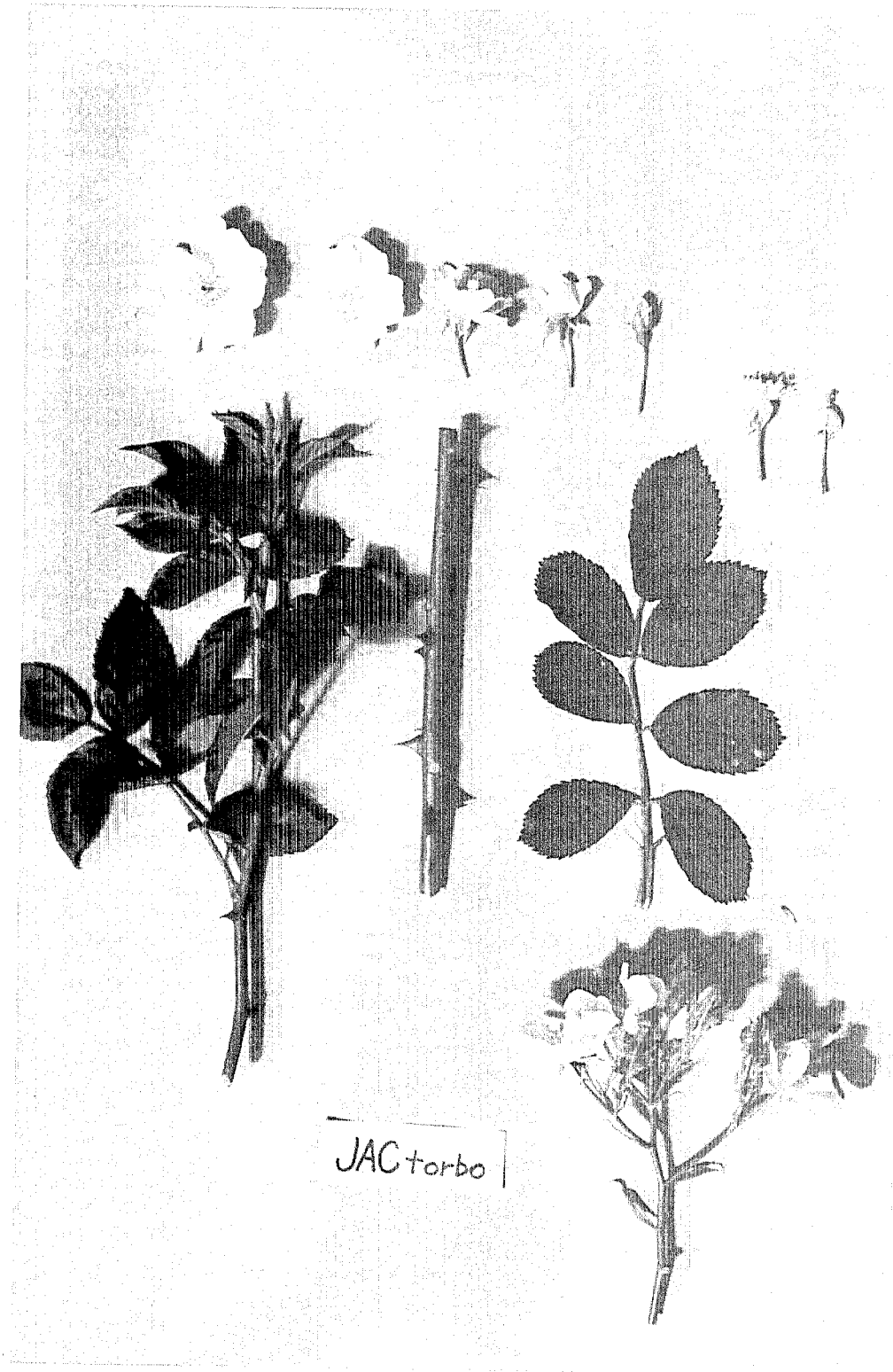
JAC torbo